(12) United States Patent
Sopori et al.

(10) Patent No.: US 8,006,566 B2
(45) Date of Patent: Aug. 30, 2011

(54) SCREENING OF SILICON WAFERS USED IN PHOTOVOLTAICS

(75) Inventors: Bhushan L. Sopori, Denver, CO (US); Peter Sheldon, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 80 days.

(21) Appl. No.: 11/722,981

(22) PCT Filed: Jul. 28, 2006

(86) PCT No.: PCT/US2006/029765
§ 371 (c)(1),
(2), (4) Date: Dec. 7, 2009

(87) PCT Pub. No.: WO2008/013547
PCT Pub. Date: Jan. 31, 2008

(65) Prior Publication Data
US 2010/0136715 A1   Jun. 3, 2010

(51) Int. Cl.
*G01L 1/24* (2006.01)
(52) U.S. Cl. ............... 73/800; 73/760; 73/777; 438/14
(58) Field of Classification Search ............... 73/760, 73/777, 800
See application file for complete search history.

(56) References Cited

U.S. PATENT DOCUMENTS

| 4,846,746 A | 7/1989 | Prost |
| 5,410,162 A | 4/1995 | Tigelaar et al. |
| 5,693,889 A | 12/1997 | Nadolink |
| 5,985,678 A * | 11/1999 | Kiyama ............................ 438/5 |
| 6,103,552 A * | 8/2000 | Lin ................................. 438/113 |
| 6,258,524 B1 | 7/2001 | Hirabayashi |
| 6,604,853 B2 | 8/2003 | Chao et al. |
| 6,734,117 B2 * | 5/2004 | Sogard .......................... 438/795 |
| 6,798,503 B2 | 9/2004 | Hiramoto et al. |
| 6,807,454 B2 | 10/2004 | Wang et al. |
| 6,816,251 B2 | 11/2004 | Swan et al. |
| 6,840,841 B2 | 1/2005 | Hakomori |
| 6,861,268 B2 | 3/2005 | Iwabuchi |
| 7,682,858 B2 * | 3/2010 | Nagai et al. ..................... 438/33 |
| 2005/0008218 A1 | 1/2005 | O'Dell et al. |
| 2005/0066739 A1 * | 3/2005 | Gotkis et al. .................... 73/760 |
| 2005/0264798 A1 | 12/2005 | Nishiyama et al. |
| 2005/0282299 A1 | 12/2005 | Kim et al. |
| 2006/0037941 A1 | 2/2006 | Weng et al. |
| 2007/0122995 A1 * | 5/2007 | Henley et al. ................. 438/455 |
| 2008/0305615 A1 * | 12/2008 | Ueno et al. .................... 438/463 |

FOREIGN PATENT DOCUMENTS

JP   11351850 A2   12/1999

OTHER PUBLICATIONS

International Search Report, PCT/US06/29765, pp. 1-4.
Mier, Graphics Script Provides Quick Classification of GaAs Wafers, Reed Electronics, Apr. 1, 2000, Reed Elsevier.
Higgs, Non-Destructive Optical Methods for Assessing Defects in Production of Si or SiGe Materials, The European Physical Journal, Feb. 10, 2004, 43-48, vol. 27.

* cited by examiner

*Primary Examiner* — Max Noori
(74) *Attorney, Agent, or Firm* — Paul J. White; Cynthia S. Mitchell; John C. Stolpa

(57) ABSTRACT

A method for screening silicon-based wafers used in the photovoltaic industry is provided herewith.

23 Claims, 5 Drawing Sheets

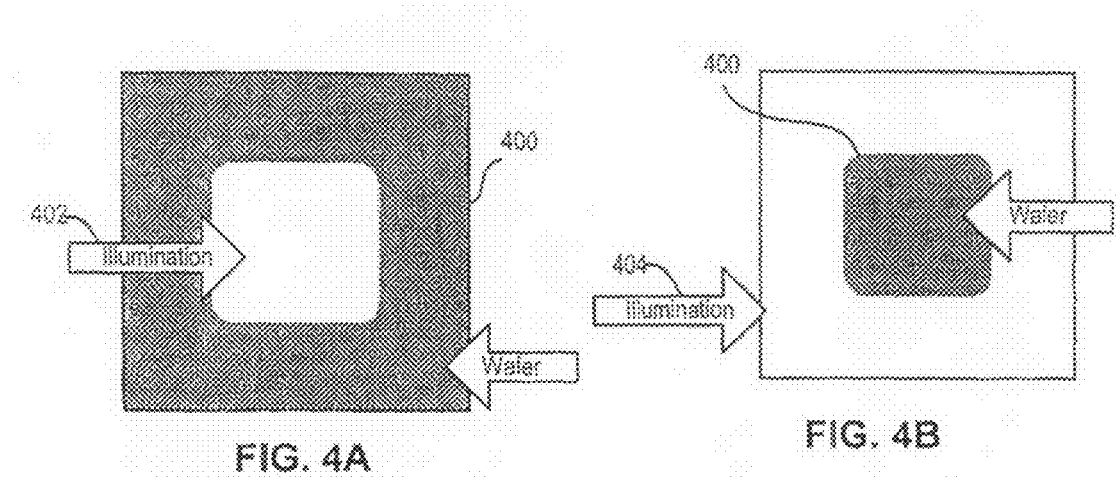
FIG. 4A
FIG. 4B
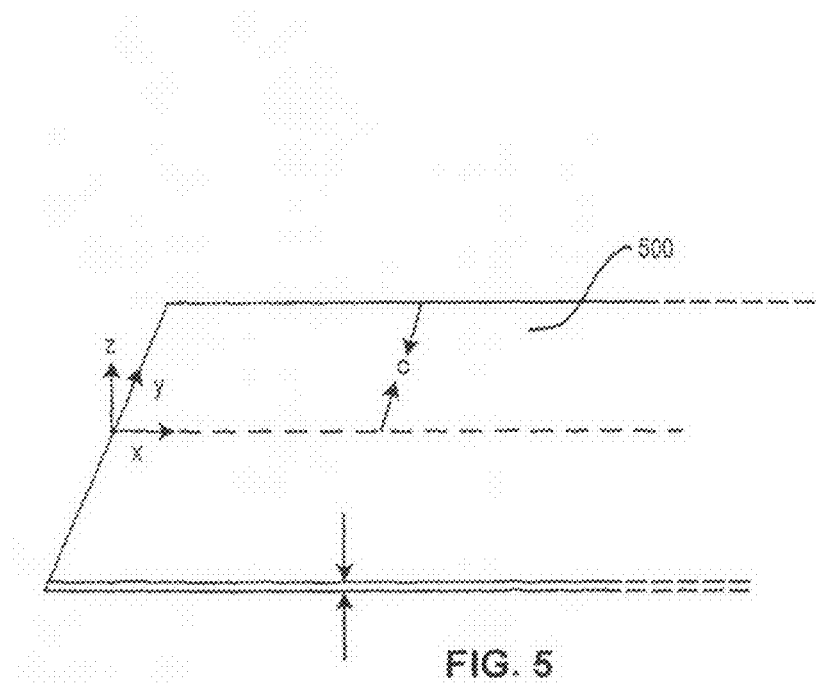
FIG. 5

SCREENING OF SILICON WAFERS USED IN PHOTOVOLTAICS

CONTRACTUAL ORIGIN OF THE INVENTION

The United States Government has rights in this invention under Contract No. DE-AC36-99GO10337 between the United States Department of Energy and the National Renewable Energy Laboratory, a Division of the Midwest Research Institute.

BACKGROUND ART

The present disclosure relates to semiconductor wafers, such as silicon wafers that are used as substrates for making photovoltaic devices.

One of the strategies for lowering the cost of silicon-based photovoltaic (PV) energy is to use thinner wafers for solar cell fabrication. This strategy reduces the wafer cost and increases solar cell efficiency, provided appropriate cell design and processing techniques are employed. Although the concept of reducing wafer thickness is quite straightforward, it is difficult to implement in manufacturing. The experience in the industry is that even for the current wafers, which have a nominal thickness of about 250 μm, the breakage during solar cell fabrication is quite high. The estimated fraction of wafers that break during cell fabrication and module encapsulation ranges between 5% and 10%. Additional reductions in the wafer thickness are found to further decrease the yield to unacceptable values.

The yield loss due to wafer breakage has a considerable influence on the economies of producing solar cells. In particular, because the loss in revenue associated with wafer breakage increases as the cell fabrication progresses, it is desirable to exclude those wafers that may break during cell processing from entering the fabrication lines. Identifying the sources of wafer breakage, understanding the wafer breakage mechanisms, and developing methods of detecting and separating these wafers that are susceptible to breakage is of value, especially at early stages of solar cell fabrication.

Wafer breakage is not a major issue in the semiconductor industry, which also uses silicon wafers. The semiconductor industry utilizes certain criteria for wafer preparation and processing, which minimize wafer breakage. These preventive measures add significant costs. The photovoltaic industry finds that it is not able to adopt these preventive measures due to the high cost that is associated with these procedures. Thus, the excessive breakage of wafers in the photovoltaic industry is primarily due to inadequate wafer preparation, inexpensive wafer handling, and low-cost device processing methods, which are all aimed at minimizing the cost of the solar cell. This incomplete wafer preparation in the photovoltaic industry leaves such as microcracks at the surfaces and the edges of the wafers, which lead to wafer breakage during cell fabrication as discussed later.

Optical methods are sometimes used in the industry to detect flaws in wafers. Japanese Patent No. JP11351850 discloses a method and apparatus for detecting a flaw on the end part of a semiconductor wafer using an optical system, which illuminates the edge and measures the scattered radiation by two detectors.

U.S. Pat. No. 6,861,268 discloses a method for inspecting a silicon wafer using a laser confocal microscope to identify and efficiently detect defects, a device fabricating process, a method for manufacturing a silicon wafer enabling manufacture of wafers not having the defect, a method for fabricating a semiconductor device using the silicon wafer not having this defect, and the silicon wafer not having the defect. When a silicon wafer is inspected, inspection is made for this new defect, having the entire defect size of 0.5 μm or more, in which microdefects gather in a colony state.

U.S. Pat. No. 6,807,454 discloses a bright field (BF) method for automatically controlling defect-specification in semiconductor manufacturing. The method provides a module to detect position, number, size, and intensity signals of defects on a processed patterned wafer. The module further compares the patterned wafer with a normal wafer to preliminarily classify the patterned wafer and creates a defect map. Then, a defect management system is provided to execute a spatial pattern recognition procedure to determine whether or not the corresponding special pattern can be recognized.

U.S. Pat. No. 6,816,251 discloses an electronic media edge defect detector in one form, having plural light sources and detectors arranged to direct and receive deflected light from the side edge margins and outer edge margins of the electronic media. The detected light is analyzed to determine the presence of defects. Individual wafers may be raised while in a cassette and turned during the inspection without removing the wafers from the cassette.

U.S. Pat. No. 6,604,853 discloses an accelerated thermal stress cycle test for semiconductor chips, which can be conducted in a reduced test time compared to the conventional test. The test is carried out in a cluster of reaction chambers that includes a CVD chamber and a cool-down chamber such that a pre-processed wafer can be heated from room temperature to at least 350° C. in an inert gas in about 2 min., and cooled down to not higher than 70° C. in a cool-down chamber in less than 30 sec. The heating and cooling steps can be repeated between 3 and 7 times to reveal any defect formation caused by the thermal stress cycle test. Typical defects are metal film peeling from insulating dielectric material layer or void formation.

The above-mentioned examples illustrate use of optical techniques to detect and identify defects or flaws in semiconductor wafers, which have polished surfaces. These techniques are difficult to use on photovoltaic wafers for detection of flaws and defects because these wafers have rough surfaces. The surface roughness "hides" such flaws and microcracks, making it difficult to recognize their presence by optical techniques. Optical excitation, as in rapid thermal processing, may also be used to heat the wafers for the purpose of wafer characterization.

U.S. Pat. No. 5,410,162 discloses an apparatus and a method for rapidly changing the temperature of a semiconductor wafer in an RTP processor in order to perform electrical tests at elevated temperature, and then cooling the wafer rapidly to ambient temperature. Electrical tests may be performed as desired during the process. Optical heating is typically employed to uniformly heat a semiconductor wafer.

Thus, it would be a significant contribution to the art to provide an effective method of rapidly screening wafers, which have defects that can result in the wafer breakage during device fabrication.

The foregoing examples of the related art and limitations related therewith are intended to be illustrative and not exclusive. Other limitations of the related art will become apparent to those of skill in the art upon a reading of the specification and a study of the drawings.

DISCLOSURE OF INVENTION

The following embodiments and aspects thereof are described and illustrated in conjunction with systems, tools and methods, which are meant to be exemplary and illustrative, not limiting in scope. In various embodiments, one or more of the problems in the above-described methods have been reduced or eliminated, while other embodiments are directed to other improvements. The present disclosure provides a method of screening semiconductor wafers with a propensity for breakage due to the presence of microcracks or other defects. The present disclosure further provides a system for use in screening wafers for use in solid state electronics, such as photovoltaic devices.

As shown in further detail by the description below, a rapid wafer screening test system presents a plurality of wafers for illumination. This may be done, for example, by placing the wafers on a conveyor belt or on a tray within an illumination chamber. The plurality of wafers contain a first set of wafers that are suitable for use in subsequent processing steps and a second set of wafers that are unsuited for use in subsequent processing steps by virtue of cracking. An optical source, such as a tungsten-halogen source, illuminates the plurality of wafers to impart a predetermined thermal stress to the plurality of wafers. This stress is such that that wafers in the second set incur substantial breakage, which may be determined as a percentage broken wafers in the second set of wafers. The wafers in the first set of wafers do not incur substantial breakage compared to percentage of broken wafers in the second set of wafers. A substantial percentage may be measured as a percentage value according to a statistically assessable quality control delimiter, such as 10%, 20%, 30%, 40%, 50%, 60%, 70%, 80% or 90% of wafers in either the first set or the second set of wafers. Although an algorithm may be used to calculate the predetermined amount of thermal stress, process parameters including, for example, conveyor belt speed and intensity of light may be used to adjust the predetermined amount of thermal stress for optimization of screening integrity.

Subsequent fabrication process steps, as are known in the art, may be used to form electronic devices, such as photovoltaic cells, on the unbroken wafers. These may include conventional chemical vapor deposition, sputtering, screen printing, spin-on deposition, electrochemical deposition, and other conventional processes to deposit materials forming any type of wafer-deposited device.

In addition to the exemplary aspects and embodiments described above, further aspects and embodiments will become apparent by reference to the drawings and by study of the following descriptions.

BRIEF DESCRIPTION OF DRAWINGS

Exemplary embodiments are illustrated in referenced figures of the drawings. It is intended that the embodiments and figures disclosed herein are to be considered illustrative rather than limiting.

FIG. 4 illustrates illumination patterns for testing mechanical strength via a) central illumination and b) peripheral illumination.

FIG. 5 illustrates a sample geometry for illustrative calculation purposes.

BEST MODE FOR CARRYING OUT THE INVENTION

This disclosure provides a method and apparatus for screening semiconductor wafers with a propensity for breakage (due to presence of microcracks and other defects). The wafers are placed on a conveyor belt, which carries the wafers through an illumination zone, and wherein each wafer receives a beam of light (under a tungsten-halogen light source). Wafers having fatal cracks may break as a result of this thermal stress, and so may be eliminated from further processing.

Figure 1:
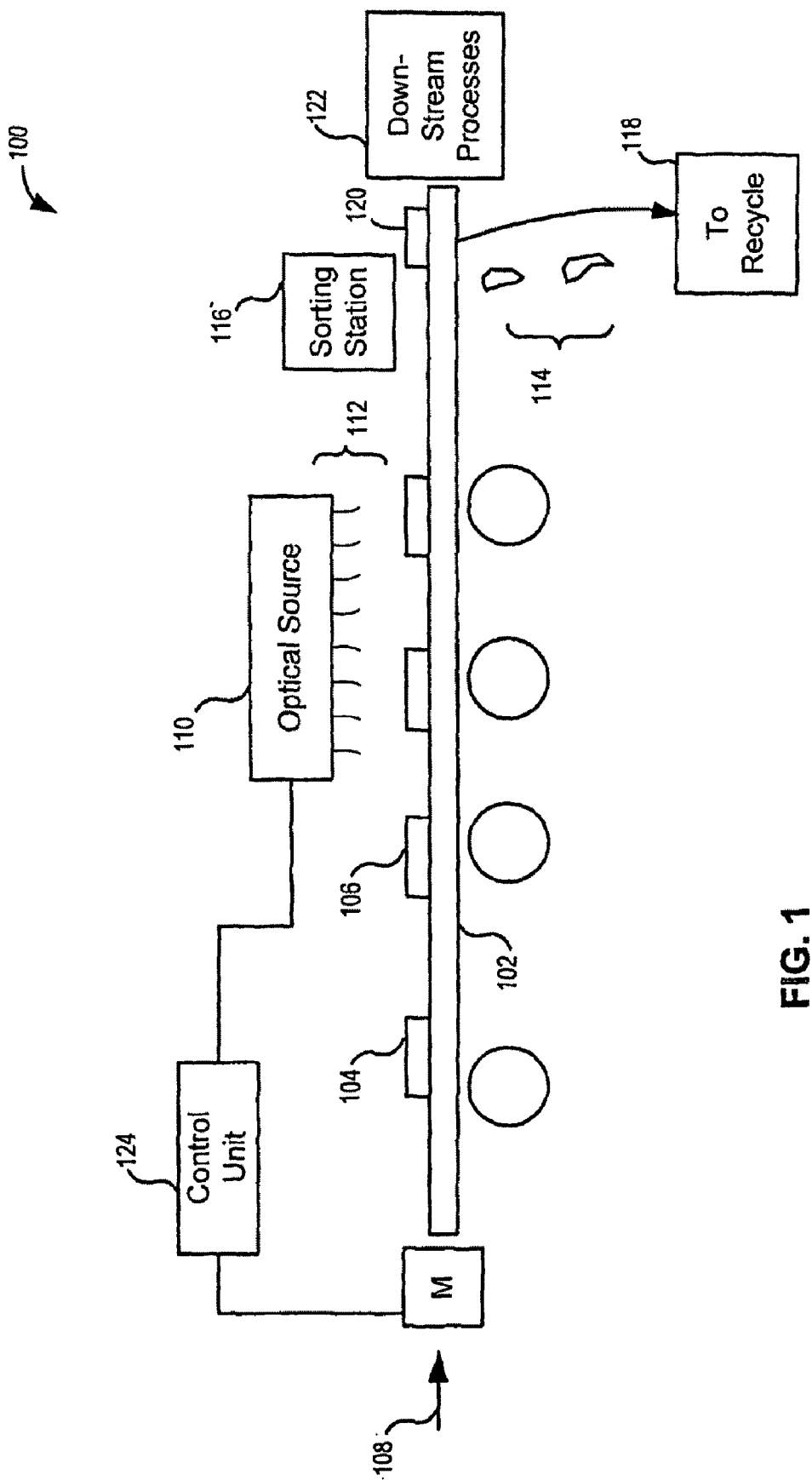
FIG. 1 is a process system schematic illustrating components of one embodiment.

As shown in FIG. 1, system 100 includes a conveyor 102 on which reside a plurality of silicon wafers 104, 106. There may be any number of such wafers, which conveyor 102 moves in direction 108 under influence of motive force M. An optical source bank 110 emits light 112 to impart a predetermined thermal stress to the plurality of wafers 104, 106. The conveyor 102 may be provided in parallel tracks (not shown) to support wafers by their edges, accordingly, defective wafers 114 are induced to break and may fall through the conveyor 102 or be removed by visual inspection at a sorting station. The defective wafers 114 may be removed to recycle 118. Wafers 120 that are suitable for use in making electronic devices may be submitted to down stream processes 122, which may be any process to form electronic devices, such as photovoltaic cells, on the wafers 120. A programmable control unit 124 may be used to govern the delivery of optical energy by adjusting such parameters as the intensity of light from the optical source bank 110 and the speed of conveyor 102. These adjustments may be used to fine tune the screening process to minimize breakage losses that would otherwise occur in the downstream processes 122.

The system 100 is used to screen a population of wafers that have a high propensity to break during a solar cell fabrication process. A predetermined thermal stress is induced in a wafer by illuminating the wafer with a narrow light beam emanating from tungsten-halogen light source. Wafers having fatal microcracks may break as a result of this stress and will be eliminated from further processing—saving the processing costs of such wafers. The broken wafers maybe recirculated as feedstock for crystal growth. Temperatures needed to establish stress levels commensurate with the breakage of wafers currently employed in the photovoltaic industry are generally moderate and maybe readily obtained for a commercial machine. This wafer-screening procedure maybe applied in the early part of the cell fabrication schedule, such as an after damage etching step. The wafers that successfully pass this test have a high probability of survival through the process. Because the survival of a wafer (with microcracks) depends strongly on the methods used for wafer transport and processing conditions, changes in wafer handling/processing conditions may change the wafer yield. The system allows such changes to be accommodated simply by changing the optical excitation levels. The proposed technique for wafer screening maybe very rapid, because for a given illumination profile, the temperature non uniformity/stress increases with increasing the wafer speed.

The present system has many advantages which include the following: 1) it is a non contact method; 2) it represents real process conditions in which parameters maybe changed to reflect changes in process conditions; 3) it is relatively easy to control the stress configuration(s); 4) it may be combined and made part of solar cell processing (e.g., could be a gettering process step); and 5) it may be easily incorporated into a wafer transport system.

A semiconductor wafer experiences stresses from a variety of sources during device fabrication. These include: 1) wafer handling, such as mechanical handling during wafer transport; 2) structure of the device, such as asymmetry in the device configuration due to depositions of dielectric and/or metallic thin films that may cause wafer loading; 3) device processing, such as stresses that are induced during thermal treatments or rapid thermal processing.

A semiconductor wafer breaks if it experiences a tensile stress exceeding the critical stress. The intrinsic critical stress for most solid materials is quite high, $\sim 10^6$ psi ($\sim 100$ Mpa). A good mechanical/thermal design of a wafer, wafer transport, and fabrication process sequence strives to limit the wafer stresses well below the critical stress values. The semiconductor industry uses design criteria for wafer preparation/handling and processing to achieve these goals. Because the mechanism of wafer breakage is that of a fracture, research has been performed in the semiconductor industry on wafer fracture. Initial studies were carried out to evaluate stress produced by various thermal profiles in conventional furnaces. These studies determined that two parameters, wafer diameter and wafer thickness, are useful when considering potential stressors. Thus, the semiconductor industry uses standardized wafer thicknesses for various wafer sizes.

Studies on metals and glasses determined that, even for a suitably selected wafer of appropriate diameter and thickness, stress levels close to intrinsic values could be reached only for "well-prepared" wafers. Other wafers fracture at stress levels well below these values. This reduction in the wafer strength was related to the surface and edge characteristics of the wafer.

The surface characteristics that may affect wafer breakage include at least shape, roughness, and surface damage. The shape of a semiconductor wafer is typically planar for other reasons. For example, based on device-processing considerations, the wafer surface must be planar and (in most cases) polished. Polishing also helps in mitigating the breakage. It has long been known that microcracks strongly control the mechanical strength of various commercial glasses. Crack-like defects act to increase the stress levels. Under uniaxial tensile loading of a material containing microcracks, the cracks begin to grow, which causes failure at stresses much below the theoretical strength. Microcracks may also exist in semiconductor wafers. Microcracks are typically generated in wafer-cutting processes such as sawing. In the semiconductor industry, cutting or sawing operations are followed by damage removal and polishing. The wafers are chemically etched to remove the damaged layer at the surface, typically 10-20 µm in thickness, and then polished on one side.

Edge Characteristics (such as shape of the edges and the technique of edge preparation) may also have significant effect on the breakage. Edge shaping typically uses a grinding process to "round off" the edges to minimize wafer breakage. Damage at the wafer edges (like surface damage) may also exist at the edges as a result of incomplete etching or edge preparation. Like surface damage, the residual edge damage may have a profound effect on the wafer strength. In some cases, the edge damage may be more harmful than the surface damage.

The semiconductor industry employs specific procedures in preparing and handling wafers to avoid breakage. These are standard procedures in wafer preparation that minimize the susceptibility of wafer breakage. Some of the wafer preparation techniques in the semiconductor industry include: 1) large wafer thickness to support unintentional stresses; 2) edge grinding; 3) wafer polishing; and 4) nearly isothermal processing. Fortunately, these criteria for minimizing wafer breakage also match criteria for making high-quality devices with a high yield. For example, wafer polishing is also necessary to achieve devices of small dimensions. Hence, wafer-preparation costs are well justified.

Wafer breakage in solar cell fabrication may be addressed as follows. Because Si solar cell processing is (in many ways) similar to microelectronic device fabrication, the Si-photovoltaic industry had initially attempted to adopt many rules observed in the semiconductor industry. Wafer preparation and processing techniques were quite similar. However, with increased production and higher demands for solar cell cost reduction, the parallelism has significantly diminished. The need for cost reduction has led to an evolution of the technologies wherein the wafers are more fragile and the breakage rates are very significant. Although the exact science for increased breakage is not known, it may be related to some of the procedures that are used in the photovoltaic industry (as summarized below).

Solar cell fabrication requires many process steps to convert an ingot of silicon into wafers and then process them into solar cells. Some of the process steps are similar to those used in the semiconductor industry. Typically, these steps include sawing, etching, formation of an N/P junction, and deposition of metallic and/or dielectric layers (some patterned and others in a blanket form). Although many process steps are performed at lower temperatures (<400° C.), some of these processes (such as phosphorus diffusion and Al alloying) are performed at elevated temperatures in which the temperature of the wafer itself may be non uniform.

Solar cell fabrication steps may be mechanically demanding on the strength of the wafer. Whereas the semiconductor industry takes adequate precautions that maintain the critical stress to near intrinsic values (to minimize wafer breakage), the photovoltaic industry cannot expend the resources/expense to suitably prepare wafers to reach the intrinsic critical stress level. The critical stresses for photovoltaic wafers are considerably smaller; the measured value of critical stress depends on the history of the wafer. Reported values of tensile critical stress are $\sim 10^3$ psi ($\sim 0.1$ Mpa or $\sim 10^8$ dynes/cm$^2$).

The major features of the photovoltaic industry that contribute to high breakage are: 1) high throughput, which demands high wafer transfer rates and faster processing times; 2) thin wafers; and 3) inadequate wafer preparation. The photovoltaic industry uses wafers that are much thinner than dictated by the semiconductor industry design rules. One reason is that thinner wafers are less expensive. The other reason is that a thinner cell may have higher efficiency (because the volume recombination is lower). Use of thinner wafers in the photovoltaic industry was also justified based on the number of process steps needed to fabricate a solar cell being a small fraction of the number of steps in microelectronics. However, thinner wafers have a lower mechanical strength. Inadequate wafer preparation may be a result of the fabrication of the solar cells on wafers with rough or textured surfaces (to enhance optical absorption). In order to minimize the solar cell cost, damage etching and texture etching are combined into one step. This process step must be properly controlled in order to minimize breakage. In this process, there are many variables. For example, the texture etching bath is difficult to control because the etch composition changes as the wafers are etched; some wafers may have incomplete damage removal; and texture etching is typically done on a surface structure developed by exposing parallel planes. Because these are cleavage planes, the textured wafer is more prone to cleavage. The preparation of solar cell wafers may change the mechanical strength of a wafer. For example, sawing is a process of material removal by fracture (in which small fragments of material are chipped away). Such a process produces damage that may propagate quite deep below the surface into the material. Another process step that alters the mechanical properties of the wafer is texture etching. Although texture etching removes the saw damage (making it less likely to break), it exposes cleavage planes of the wafer, making them more likely to break in handling. Thus, cell processing itself may influence the state of stress in the wafer, which may change the propensity of the wafer toward breakage.

In the wafer processing, the steps employed may include the following: 1) sawing: this introduces stresses that may make the wafer/cell more susceptible to breakage; 2) texturing: this produces changes in the wafer morphology that may enhance the wafer breakage; and 3) little or no edge preparation which is of particular concern for ribbons.

Residual stresses may also contribute, to breakage. In addition to the characteristics of the wafer, aspects of the solar cell design may make it prone to the generation of mechanical stress in the device. For example, the metallization of solar cells occupies a large area of the device (typically, 8% of the front and nearly 100% on the back side). The photovoltaic industry strives to optimize cost-effectiveness by minimizing the wafer breakage, particularly toward the later part of the device fabrication. During the early processing, there is considerable interest in understanding wafer-breakage mechanisms and trying to minimize wafer breakage. In non-isothermal processing, the photovoltaic industry uses belt furnaces for infrared heating of wafers. To minimize the equipment and process costs, the temperature uniformity of the wafer is a minor consideration.

Microcracks are believed to be the dominant sources that reduce the critical stress below the intrinsic values and lead to early breakage of wafers. Microcracks are typically generated in wafer cutting processes, such as sawing and laser cutting. In most cases, cutting or sawing operations are followed by damage removal (consisting of etching away the damaged layer at the surface, typically 10-20 µm in thickness). In some cases, the microcracks may be deep enough that they are not removed by etching. The residual microcracks may be the sites where wafer cleavage initiates, which may result in wafer breakage. Saw damage exists at the wafer surfaces as well as at the edges. In some cases, edge damage may be more harmful than surface damage. The edge shape may also have a significant effect on the breakage. The microelectronics industry uses edge shaping to minimize the wafer breakage. Edge shaping is typically a grinding process to "round off" the edges.

As the wafers go through various process steps in solar cell fabrication and encapsulation, they are transported via cassettes, conveyor belts, suction cups, and other robotic devices. Because the photovoltaic industry has a very high throughput, wafer handling and transport are done very rapidly.

As described above, wafer breakage occurs as a result of external stress applied in a direction that causes one or more of the following: 1) added residual stress, increasing stress levels beyond the critical stress; and 2) microcracks. Breakage due to item 1 was a major problem in the early years of casting and ribbon growth. In both of these technologies, the material was heavily stressed to the extent that cast ingots would break during sawing and ribbons would buckle heavily. These wafers readily broke during solar cell processing. The photovoltaic industry has developed better control of thermal profiles during crystal growth, which minimize the residual stresses in the wafers. The majority of the thermal stress generated during crystal growth results in a plastic flow in which the material yields to produce crystal defects such as dislocations. In the current solar cell processing, a process step that causes significant stress (to the extent that wafers buckle and break) happens during metallization. The stress induced in this process step may be reduced by (i) reducing the back coverage of the metal, (ii) designing gridded front and back patterns (which may be aligned in different directions), and (iii) minimizing the metal thickness (mass). The dominant reason for breakage appears to be due to the presence of microcracks.

The following analyses of a microcrack present in a photovoltaic wafer uses the Griffith crack analysis in glass, where the breaking strength $\sigma_c$ in tension due to a microcrack of a (2c) length, may be written as follows:

$$\sigma_c = (2\gamma E/\pi c)^{1/2}$$

"γ" is the specific surface energy of the material, and E is the Young's modulus. This expression may be approximated as:

$$\sigma_c = [E/20] \times (a/c)^{1/2}$$

"a" is the atomic radius. Thus, it is seen that the larger the crack, the lower the strength of the wafer. From this equation, the critical stress required for different crack sizes may be estimated. Using a "reasonable" value of $E=1.17\times10^{12}$ dynes/cm$^2$, a=5.43 Å. Hence, $$\sigma_c \sim [1.17\times10^{12}/20] \times (10.9\times10^{-4})^{1/2} \text{ dynes/cm}^2$$

$$\sigma_c \sim 3.5\times10^{10} \text{ dynes/cm}^2, \text{ if the crack is 1 µm in length}$$

For a crack of 100 µm in length, the critical stress will be reduced by a factor of 10, to $3.5\times10^9$ dynes/cm$^2$.

Figure 2:
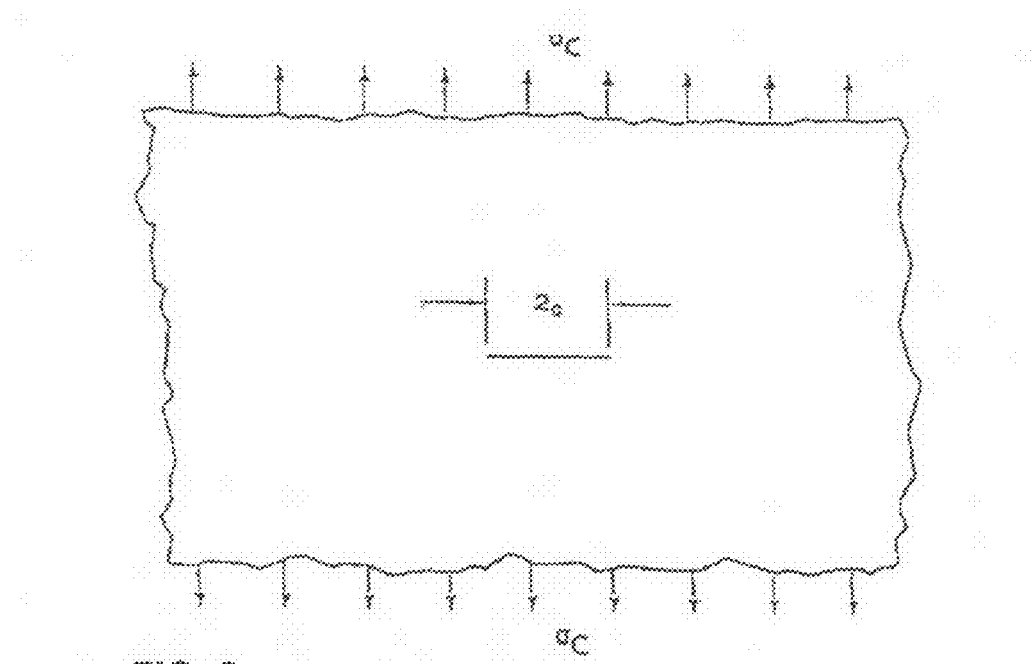
FIG. 2 illustrates a tensile stress crack.

FIG. 2 illustrates a tensile critical stress normal to the crack.

The above calculation identifies the range of maximum stress levels that must be reached in a process that may break a wafer. As provided below, stress levels may be reached at reasonably low temperatures by suitably designing the temperature profiles.

Although wafer breakage is a serious problem in the photovoltaic industry, the current techniques employed for the prevention of breaks are not cost effective. Some techniques are currently being used to directly observe cracks in solar cell wafers and devices.

Infrared (IR) imaging is used to determine precipitates and other defects in Si. Typically, IR imaging requires a double-sided polished wafer through which an IR beam is passed and its local transmission observed. Like a precipitate, any discontinuity in a wafer will alter the IR transmission. Thus, it is expected that a crack may produce an increased transmission when a small beam illuminates the region in the vicinity of a crack. Unfortunately, photovoltaic wafers are not polished. The wafers have rough or textured surfaces for good antireflection and light-trapping properties. IR imaging may have some use in ribbon wafers because their surfaces are somewhat shiny (but they have thickness striations and global variations). Because ribbon wafers are laser cut, this technique may have some application in identifying edge cracks in the ribbons.

Microcracks may appear anywhere in a single-crystal or cast me-Si wafer. It is difficult to image cracks due to the small size.

Thermal imaging may also be employed in monitoring defects in wafers. A crack produces discontinuity in the thermal impedance of the wafer. Hence, if a wafer is heated, there will be a temperature discontinuity at the crack site.

A problem in imaging a crack is that microcracks are typically small. It is difficult to select wafers based on the detection of microcracks. Although imaging cracks and microcracks may be useful to study their origin and other behavior, it is not easy to relate the presence of microcracks to wafer breakage. For example, wafers with microcracks may easily survive certain processes that are "gentle" (produce very little stress) or if they may be handled in suitable ways. A more appropriate approach to deal with the problem of cracks in substrates is to determine if a wafer (produced by a given processing condition) is likely to break during a set of processing and handling conditions. It is generally sufficient to determine if the presence of cracks will lead to a failure of the wafer during cell fabrication. A reasonable approach has been to identify wafers that are likely to break during the solar cell processing and remove them.

One way to determine if a wafer will break in a given process sequence is to simulate the stresses/stress-distributions (or the most stringent distribution) that the wafer will experience during that process. A standard method to determine critical stress is to apply a local tensile stress to a wafer until it fractures. A well-known approach consists of three-point loading, wherein the applied stress is increased until the wafer breaks. In a typical application, three-point loading is applied on a local region. This approach is good for double-sided polished wafers free from surface defects. When defects are present, the measured critical stress may depend on whether the measurement region contains surface defects.

Stress may be applied stress to the entire wafer. However, a mechanical means of applying stress to the whole wafer is not convenient (for example, wafers may not have the same thickness or the wafers may not be uniform in thickness). Applying stress requires an elaborate means of both holding the wafer and a means of applying the stress. In particular, it is difficult to control the mechanical stress if the wafer is warped or does not have uniform thickness.

A method for testing the propensity of a wafer to break in typical solar cell processing that overcomes the difficulties of applying mechanical stress may be employed. This technique is a noncontact method. The basic principle of this approach is to apply suitable stresses to a wafer with a predetermined configuration representative of solar cell processing/handling conditions. If the wafer breaks during this testing, the wafer is automatically pulled out of the processing line to save further processing costs. Another objective of this method is to select wafers for further analyses that may identify reasons for wafer breakage.

The method of the current disclosure creates a stress distribution in the wafer by imposing a thermal profile through an optical excitation. The process consists of heating a wafer in a non-uniform manner to generate predetermined stresses.

Figure 3:
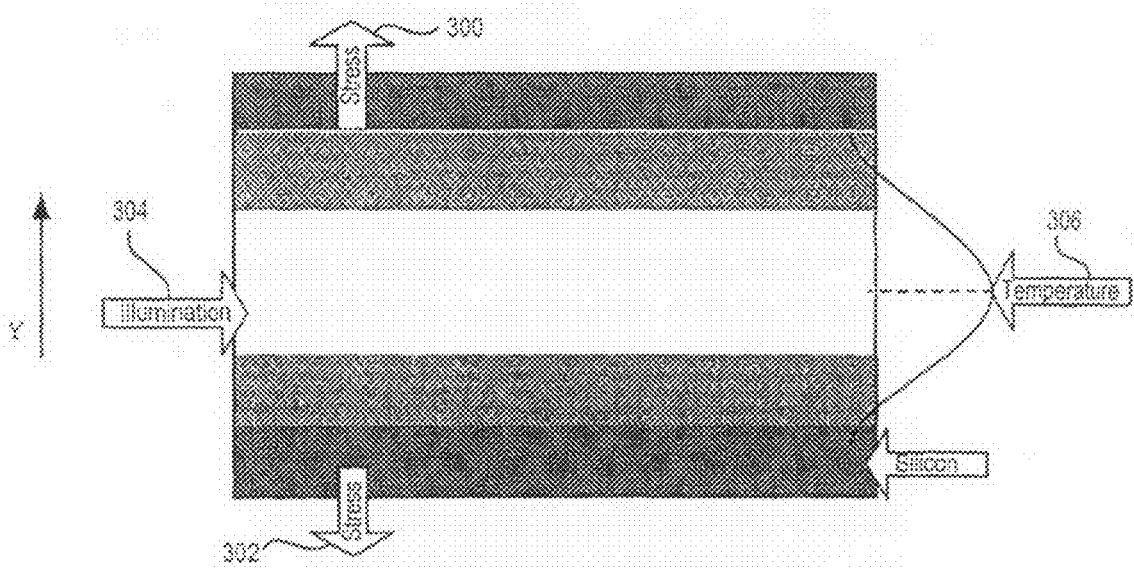
FIG. 3 illustrates a temperature gradient produced by optical linear illumination.

FIG. 3 illustrates generation of thermal stress 300, 302 due to a laterally uniform illumination 304, 306. Instead of using mechanical stress (such as bending) to introduce tensile stress, thermal stress may be introduced by optical heating. In FIG. 3 is illustrated a simple means of creating stress in the wafer. The wafer is partially illuminated with absorbing light, such as that from a tungsten halogen lamp or a bank of lamps. Typical light intensity is in the range of 4-10 W/cm$^2$, which may produce local wafer temperature in the range of 400°-1000° C. Because of the partial illumination, the wafer will acquire a temperature distribution, as qualitatively illustrated in FIG. 3. This temperature distribution will in turn lead to stresses. The illumination of FIG. 3 will generate a compressive stress in the illuminated region of the wafer and tensile in un-illuminated regions. The amplitude of the stress depends on the intensity distribution of the light (based on some simple assumptions), which dictates the temperature distribution. The stress developed in the wafer is a function of non-linearity in the temperature gradient as well as the maximum temperature. The temperature distribution itself (of the wafer) is determined by the incident flux distribution and the convection flow. Here we will show that the temperature range required to produce desirable levels of stress are quite reasonable and the equipment needed to induce such stress levels may be quite simple and inexpensive.

The stress developed may be determined through calculation using the following bi-harmonic equation (with appropriate boundary conditions):

$$\nabla^4\phi = \alpha E \nabla^2 T$$

$\phi = \phi(\in_{ij}, T)$ is the free-energy function, $\alpha$=thermal expansion coefficient, E•=modulus of elasticity, $\in_{ij}$=small-strain tensor, and T=temperature.

The illumination pattern illustrated in FIG. 3 is a basic configuration that produces a predominantly one-dimensional stress (if free edges are ignored). In a practical wafer, the microcracks may be located along any direction. More suitable illumination configurations are shown in FIGS. 4A and 4B. The objective of the illumination pattern is to produce a stress distribution most suitable for simulating the nature of stresses within the fabrication schedule of a given manufacturing company.

FIG. 4 provides illumination patterns for testing mechanical strength of a square wafer 400 that may be used for solar cell fabrication including: 4A central illumination 402, and 4B peripheral illumination 404.

As an illustration (to acquire an insight into the behavior of stresses), a simple case of a rectangular sample 500 is considered (FIG. 5) of width 2C, whose length is much larger than the thickness (this assumption makes thickness components of stress to be negligible as compared to in-plane components, i.e., $\sigma_{zz}=\sigma_{xz}=\sigma_{yz}=0$).

Equation 2 may be written as $$\partial^4_x\phi + 2(\partial^2_x\partial^2_y)\phi + \partial^4_y\phi = -aE(\partial^2_x T + \partial^2_y T)$$

with $$\sigma_{xx}=\partial^2_y\phi \; \sigma_{yy}=\partial^2_x\phi \; \sigma_{xy}=\partial^2_{xy}\phi$$

The boundary conditions are: Boundaries are free at X=0, and Y=±C, i.e., all the stress components normal to the boundaries must vanish.

$$\phi = \partial_n \phi = 0$$

The general trends of the stress distributions may be analyzed by examining approximate solutions. For example, if we assume that temperature distribution at X=L (L=length of the sample) is slowly varying, a simple expression for $\phi$ may be expressed as:

$$\phi(L,Y) \sim (-\alpha E/24)(Y^2-C^2)^2(\partial^2_x T)$$

The above equation gives a physical insight into the distribution of stress in the wafer. In many cases one can use a finite element modeling package to determine stress distributions. FIG. 5 provides a sample geometry for illustrative calculation. The sample is illuminated by a light source that leads to a steady-state temperature distribution. FIG. 5 illustrates the typical stresses produced by such excitation.

Figure 6:
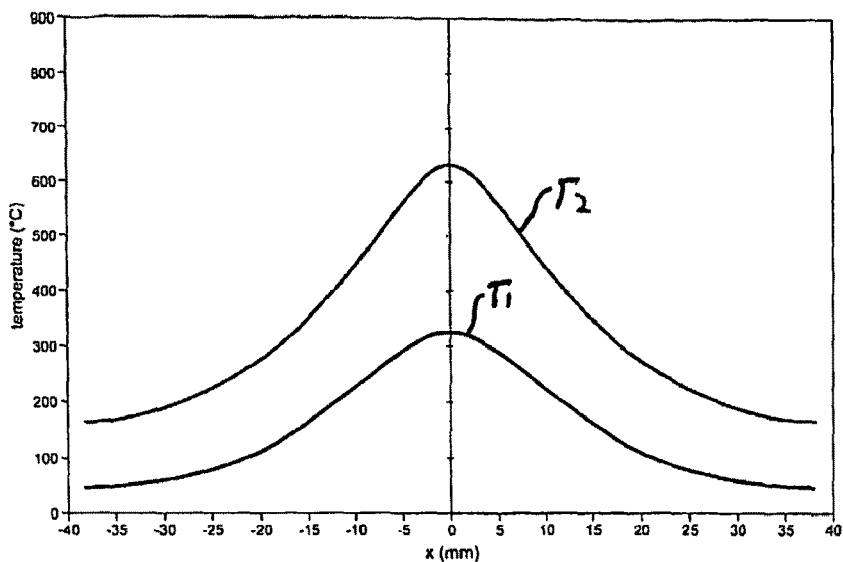
FIG. 6 illustrates two temperature distributions used to illustrate stresses produced in a square wafer typically used for solar cell fabrication illuminated by a linear light distribution.
Figure 7A:
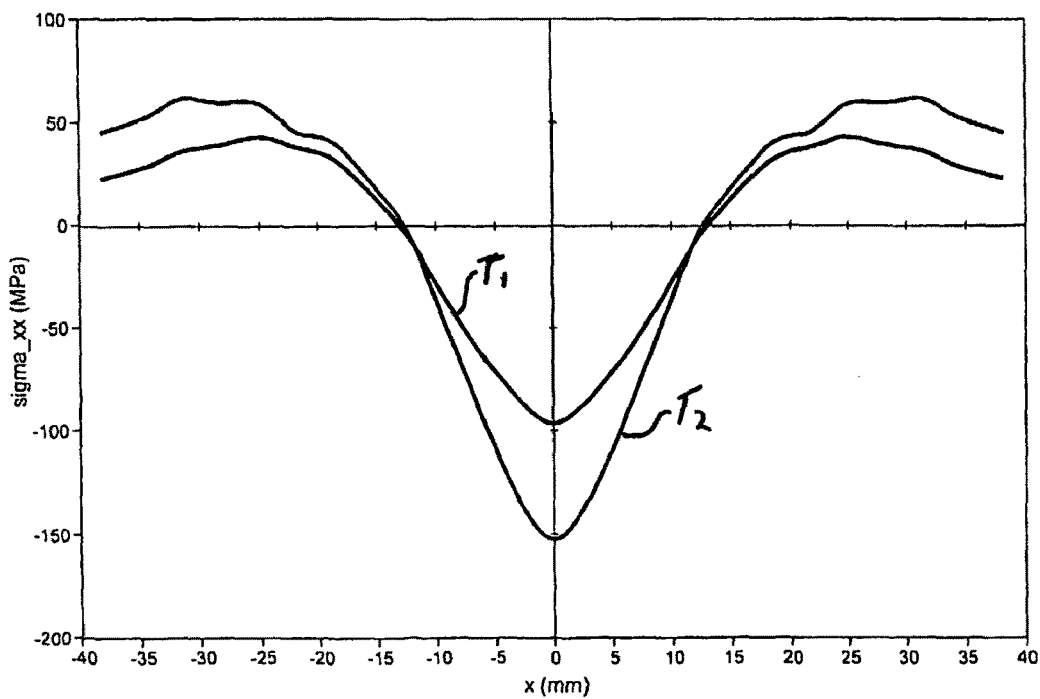
FIG. 7 illustrates calculated stress distributions $\sigma_{xx}$ and $\sigma_{yy}$ along X direction at Y=0 as a function of wafer position.
Figure 7B:
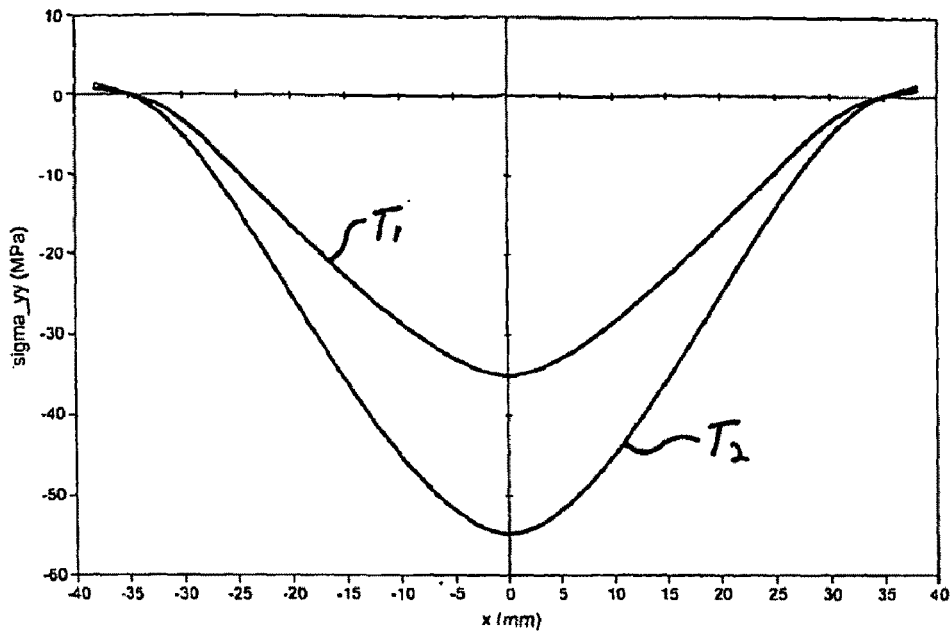

Two temperature distributions are considered, as shown by $T_1$ and $T_2$ of FIG. 6, which are used to illustrate stresses produced in a narrow wafer illuminated by a light source. Each of these temperature distributions has a maximum at X=0 mm. These temperature distributions are typically used for growth of Si ribbons, and are capable of minimizing stress during ribbon growth. In practice, the above temperature distributions are difficult to obtain. It is much easier to obtain temperature distributions that have large non-linear gradients. FIG. 6 provides two temperature distributions FIGS. 7A and 7B provide calculated stress distributions $\sigma_{xx}$ (FIG. 7A) and $\sigma_{yy}$ (FIG. 7B) along Y=0 for a Si wafer for temperature profiles $T_1$ and $T_2$ of FIG. 6.

Stress values in excess of 100 MPa ($10^{11}$ dynes/cm$^2$) may be reached at relatively low temperatures. Some features of the stresses generated are: 1) The stress is determined primarily by the temperature non-linearities and not the absolute magnitude of the temperature. 2) Stress values reach $10^8$ dynes/cm$^2$ (values in the range of critical stresses for breakage). 3) The induced stresses increase with an increase in the wafer width.

The temperature distributions of FIG. 7 show that $\sigma_{xx}$ and $\sigma_{yy}$ are both compressive at Y=0.

The following Example illustrates the practice of the present instrumentalities.

Example 1

Figure 8:
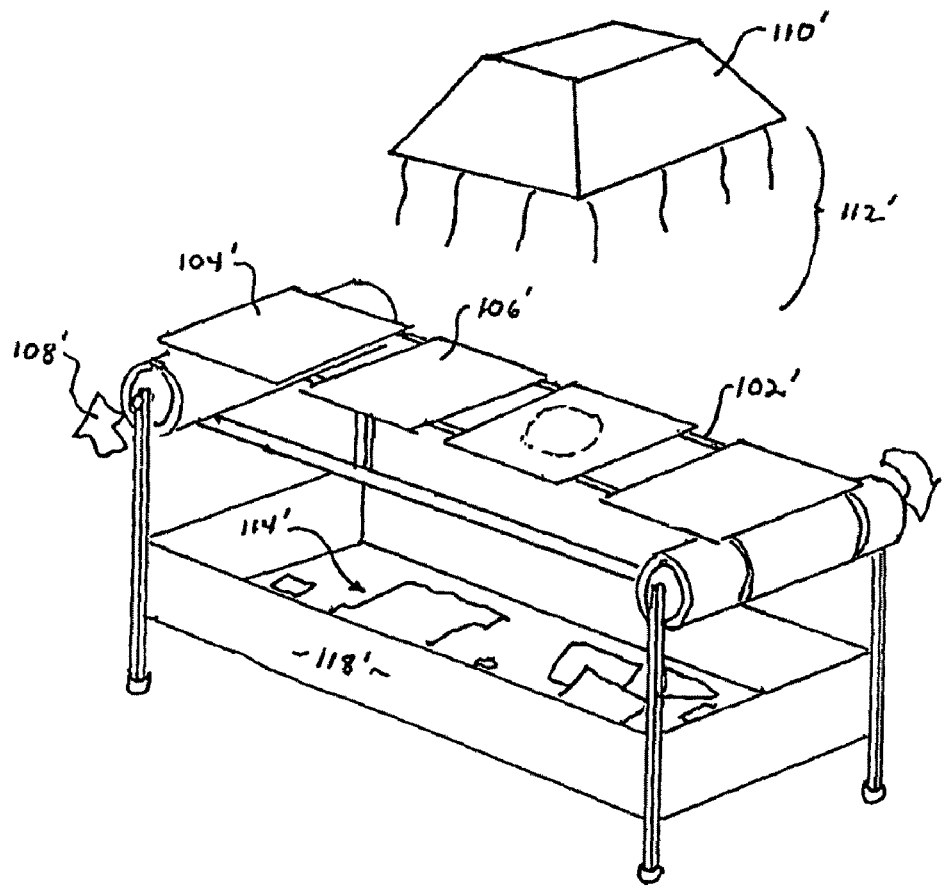
FIG. 8 illustrates a simple setup for isolating problem wafers using thermally-induced stress.

The practical implementation of the above principles may easily be performed in a system consisting of a light source and a conveyor belt arrangement as shown in FIG. 8, which shows a schematic of a simple setup for isolating wafers likely to break during solar cell processing. Since the embodiment shown in FIG. 8 is representative of the system 100 shown in FIG. 1, like numbering of identical parts is designated by a "'", such as system 100' of FIG. 8.

The wafers are sequentially placed on a belt, which preferably supports the wafers at the edges. They are conveyed into a region which has a narrow illuminated zone. As the wafers pass under this illumination, each wafer acquires a temperature-distribution, which depends on the intensity pattern of the light, the size of the wafer, and the belt speed. This results in a predetermined thermal stress.

As a result of non-uniform heating, a stress distribution is induced in the wafer. The illumination pattern is chosen to simulates the stress levels commensurate with the process conditions (for a given solar cell sequence). The illumination pattern for a given belt speed may be calculated using theoretical analysis. Such a calculation involves: (i) determination of the temperature profile of the wafer for a given illumination pattern, and (ii) using this temperature profile to calculate dynamic stress distribution in the wafer.

The illuminated zone may be established using light sources such as tungsten-halogen lights with suitable reflectors and masks. Any suitable light source which provides the desired illumination may be employed. The illumination distribution is typically adjusted such that the induced stress levels are below the critical stress values for wafers that have small or no microcracks, and above the critical level for "large" microcracks. In the illumination zone, the wafers may be convection cooled to tweak the temperature non-uniformities needed to acquire stresses of the magnitude identified in this disclosure. Such convection cooling may be performed by flow of gases directed by suitable nozzles. The power controller that energized the light source may control the exact level of stress. Thus, wafers with cracks that may be fatal for a solar cell process, will break during their travel through the illuminated zone. The broken wafers are likely to lose the support form the belt and fall into a collector below, or may be mechanically removed when they exit the machine.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of screening a wafer, which comprises:
   presenting a plurality of wafers for illumination, wherein the plurality of wafers contain a first set of wafers that are suitable for use in subsequent deposition steps and a second set of wafers that are unsuited for use in subsequent deposition steps by virtue of cracking;
   illuminating the plurality of wafers with a light source that imparts a predetermined thermal stress to the plurality of wafers such that the wafers in the second set of wafers incur substantial breakage determined as a percentage of broken wafers in the second set of wafers and the wafers in the first set of wafers do not incur substantial breakage determined as a percentage broken wafers in the second set of wafers; and
   as a result of the illuminating step, selectively breaking the wafers of the second set of wafers.

2. The method of claim 1 wherein the step of illuminating proceeds while the wafer resides on a conveyor belt.

3. The method of claim 2 further including adjusting a speed of the conveyor belt to tune the step of illuminating.

4. The method of claim 3 wherein the step of illuminating includes adjusting a speed of the conveyor belt to provide sufficient time for illumination of the wafer according to a type of light source that is used and the amount of predetermined thermal stress to be delivered to the wafer.

5. The method of claim 1 further including a step of calculating the predetermined thermal stress that in the step of illuminating is delivered to the plurality of wafers on the basis of an algorithm that assesses the critical stress value for breakage based upon microcracks.

6. The method of claim 1 wherein the step of illuminating is performed sequentially on the plurality of wafers.

7. The method of claim 1 wherein the step of illuminating is performed simultaneously on the plurality of wafers.

8. The method of claim 1 wherein a light source used in the step of illuminating comprises a tungsten halogen light source.

9. The method of claim 1, further including a step of recirculating broken wafers as feedstock for use in wafer production.

10. The method of claim 1, wherein the plurality of wafers used in the step of presenting are silicon wafers.

11. The method of claim 1, further including a step of depositing layers of unbroken wafers of the plurality of wafers to form an electronic device.

12. The method of claim 11, wherein the step of depositing additional layers forms a photovoltaic cell.

13. A system for screening a wafer, which comprises:
   means for presenting a plurality of wafers for illumination, wherein the plurality of wafers contain a first set of wafers that are suitable for use in subsequent deposition steps and a second set of wafers that are unsuited for use in subsequent deposition steps by virtue of cracking; and
   means for illuminating the plurality of wafers with a light source that imparts a predetermined thermal stress to the plurality of wafers such that that wafers in the second set of wafers incur substantial breakage determined as a percentage of broken wafers in the second set of wafers of the and wafers in the first set of wafers do not incur substantial breakage determined as a percentage of broken wafers in the second set of wafers.

14. The system of claim 13 wherein the means for presenting includes a conveyor belt to advance the plurality of wafers under illumination.

15. The system of claim 14 further including means for adjusting a speed of the conveyor belt to tune the means for illuminating.

16. The system of claim 15 wherein the means for adjusting includes means for adjusting a speed of the conveyor belt to provide sufficient time for illumination of the wafer according to a type of light source that is used and the amount of predetermined thermal stress to be delivered to the wafer.

17. The system of claim 13 further including means for calculating the predetermined thermal stress that the means for illuminating delivers to the plurality of wafers on the basis of an algorithm that assesses the critical stress value for breakage based upon microcracks.

18. The system of claim 13 wherein the means for illuminating includes means for sequentially illuminating the plurality of wafers.

19. The system of claim 13 wherein the means for illuminating includes means for simultaneously illuminating the plurality of wafers.

20. The system of claim 13 wherein the means for illuminating includes a tungsten halogen light source.

21. The system of claim 13, further comprising the plurality of wafers as silicon wafers.

22. The system of claim 1, further including means for forming layers on unbroken wafers of the plurality of wafers to provide an electronic device.

23. The method of claim 12, wherein means for forming additional layers includes means for forming a photovoltaic cell.

* * * * *